(12) United States Patent
Loparic et al.

(10) Patent No.: US 9,746,493 B2
(45) Date of Patent: Aug. 29, 2017

(54) SAMPLE HOLDER FOR AN ATOMIC FORCE MICROSCOPE

(71) Applicant: UNIVERSITAT BASEL, Basel (CH)

(72) Inventors: Marko Loparic, Basel (CH); Pascal Alexander Oehler, Buchs (CH)

(73) Assignee: University of Basel, Basel (CH)

( * ) Notice: Subject to any disclaimer, the term of this patent is extended or adjusted under 35 U.S.C. 154(b) by 0 days.

(21) Appl. No.: 14/902,608

(22) PCT Filed: Jul. 5, 2014

(86) PCT No.: PCT/EP2014/064389
§ 371 (c)(1),
(2) Date: Jan. 4, 2016

(87) PCT Pub. No.: WO2015/001119
PCT Pub. Date: Jan. 8, 2015

(65) Prior Publication Data
US 2016/0187375 A1   Jun. 30, 2016

(30) Foreign Application Priority Data
Jul. 5, 2013   (EP) .................................... 13175439

(51) Int. Cl.
*G01Q 30/20*   (2010.01)
*A61B 10/02*   (2006.01)
*G01Q 60/24*   (2010.01)

(52) U.S. Cl.
CPC ......... *G01Q 30/20* (2013.01); *A61B 10/0233* (2013.01); *G01Q 60/24* (2013.01)

(58) Field of Classification Search
USPC ....................................... 850/18, 33; 73/105
See application file for complete search history.

(56) References Cited

U.S. PATENT DOCUMENTS

| 5,103,095 A * | 4/1992 | Elings | G01Q 10/04 |
| | | | 250/307 |
| 8,371,182 B1 * | 2/2013 | Israelachvili | G01N 3/04 |
| | | | 356/244 |
| 2008/0163702 A1 * | 7/2008 | Sunwoldt | B82Y 35/00 |
| | | | 73/864.91 |

FOREIGN PATENT DOCUMENTS

| EP | 1950764 | 7/2008 |
| WO | WO2006/012893 | 2/2006 |
| WO | WO2007/021903 | 2/2007 |

\* cited by examiner

*Primary Examiner* — Kiet T Nguyen
(74) *Attorney, Agent, or Firm* — JMB Davis Ben-David (57) ABSTRACT

The present invention relates to sample holders for holding a sample, particularly for an atomic force microscope. Such a sample holder comprising a sample dish (1) comprising a bottom (2), and an opening (3) arranged in said bottom (2) for receiving and holding the sample (15). Furthermore the present invention relates to a sample holder system and to a method for transferring an e.g. biological sample (15) from a biopsy tool (18) to a sample holder.

14 Claims, 6 Drawing Sheets

SAMPLE HOLDER FOR AN ATOMIC FORCE MICROSCOPE

CROSS-REFERENCE TO RELATED APPLICATIONS

This is the U.S. National Stage of International Application No. PCT/EP2014/064389, filed Jul. 5, 2014, which was published in English under PCT Article 21(2), which in turn claims the benefit of EP Patent Application No. 13175439.2, filed Jul. 5, 2013.

The present invention relates to a sample holder for an atomic force microscope (AFM), a sample holder system as well as a method for transferring a sample from a biopsy tool to a sample holder.

Today AFM (atomic force microscopy/microscope) is recognized as a very promising and important tool for exploring in vivo and/or in vitro of variety of biological processes and pathologies. However, working with living biological tissues requires specific experimental settings to ensure their viability and consequently accurate and reproducible measurements. These settings include: 1) fast and easy sample transfer from the extraction site to the AFM, 2) firm and easy sample attachment, and 3) near physiological experimental conditions (gas, temperature and perfusion). Presently, samples are often transferred in provisional tubes or boxes to the labs and are then attached with glue to a sample holder.

However, this may cause several problems. It is for instance known that the biological sample needs to be immersed continuously in the appropriate buffer solution (i.e. an aqueous solution consisting of a mixture of a weak acid and its conjugate base or a weak base and its conjugate acid, so that its pH-value changes very little when a small amount of strong acid or base is added to it) to maintain its physiological functions. It is furthermore known that most of the frequently used glues (e.g. Epoxy, Tissue Glue) do not perform properly in liquid environment. Consequently, biological samples often need to be partially dried which could significantly alter their properties. Moreover, mixing of the glue with the sample buffer could potentially contaminate the sample.

Furthermore, biological samples are usually very soft and quite small if extracted by means of a biopsy tool. When such a sample is transferred from the tool to a provisional tube/box, the risk of damaging the sample increases since it is not fastened but freely floating in a buffer solution which complicates further handling. Taking the sample out of such a provisional box and positioning said sample for analysis under the AFM manually increases the risk of damage as well.

Despite many improvements and upgrades of AFM devices and setups over the last decade, little has been done for improving e.g. a firm fastening, a thorough hydrating and/or the positioning procedure of tissue samples even though such improvements are the prerequisite steps for stable, fast and accurate AFM measurements. Current protocols are limited to a number of different gluing procedures on usually hydrophobic (Teflon) materials or in dish (Petri dish) holders. Gluing is potentially affecting the measurements as the glue mixes with the tissue (e.g. Tissue glue) or with the buffer (e.g. Epoxy glue) which could potentially contaminate the sample surface. There are certain protocols which are overcoming those problems but are usually handling- and time consuming.

Based on the above, the problem underlying the present invention is to provide a sample holder, a sample holder system as well as a method for transferring a sample from a biopsy tool to a sample holder that allows for an improved handling of the respective sample.

This problem is solved by a sample holder described herein. Preferred embodiments are stated in the sub claims and are described below.

Further, the problem underlying the present invention is solved by a system and a method described herein.

As described herein, said sample holder comprises a sample dish comprising at least a bottom, as well as an (e.g. through-) opening arranged in said bottom, particularly in its center, for receiving and holding a sample.

Here, particularly, the opening for holding the sample has a similar diameter or cross-sectional shape as the sample to be received. The mechanism for holding the sample originates particularly from a mechanical force acting as a clamping force on the sample when arranged in said opening. Particularly, the inner diameter of the opening may also be reduced by a means for reducing said inner diameter, so as to clamp the sample in said opening (see also below).

Applying such kind of a holding mechanism to the sample makes the use of glue, such as e.g. epoxy, obsolete, as the holding mechanism is using glue-free mechanical stabilization of the sample to avoid potential glue contamination of the sample, particularly either because of mixing glue with the sample or with a surrounding buffer solution. Moreover, mechanical stabilization is providing the possibility to use the same sample after performing e.g. an AFM measurement on the sample for further analysis, since the composition and structure of the sample is not compromised by chemicals stemming from the gluing procedure or the glue itself. Mechanical stabilization also takes less time as compared to gluing, as there is no need to wait for glue curing. Furthermore, the sample holder according to the invention may hold all kinds of samples such as cartilage, bone, breast tissue, skin tissue, blood vessels, bladder etc.

Preferably, said opening is defined by a circumferential first wall of said bottom that is particularly designed to clamp said sample when the sample is received by or inserted into said opening.

In another variant, a circumferential wall of said opening is at least in sections formed out of a material, e.g. a hydrophilic polymer, which expands in contact with water or a buffer solution so that the inner diameter of said opening decreases resulting in clamping of the sample, when brought into contact with water/buffer solution. Further, preferably, the sample dish, i.e., its bottom, comprises a recess delimited by a circumferential second wall of the bottom and said first wall, wherein particularly said second wall encompasses said first wall.

Particularly, said recess is designed to receive a connection portion of a sample stage of an atomic force microscope, for fastening the sample holder to the sample stage. Such a sample stage is used with an atomic force microscope for positioning the sample under the AFM tip. Usually, two kinds of stages are found in AFMs. One kind of stage is designed to be displaced below the AFM tip, whereas the other kind remains at a fixed position and the AFM tip is scanned along the sample. In each case, the sample holder is fixed to the sample stage and does not move with respect to the sample stage when scanning the sample.

Furthermore, particularly, said recess is designed to receive a connection portion of a biopsy tool, wherein said biopsy tool is designed for collecting the sample and transferring said sample to the sample holder. The connection portion of the biopsy tool and the sample stage are preferably identical at least in sections so that both can be inserted into the recess and thereby fastened to the sample holder. Particularly, the sample holder is first connected to the biopsy tool for transferring the sample to the sample holder. Thereafter, the biopsy tool is removed from the sample holder and the sample holder is fastened to the sample stage of the AFM.

Preferably said second wall comprises an inner side, wherein said inner side particularly comprises an (internal) thread for fastening the connection portion of the sample stage and/or the connection portion of the biopsy tool, wherein particularly said connection portions comprises an (external) thread, respectively, matching said internal thread, such that the connection portions can each be screwed in the internal thread of said recess. Of course, other suitable connection mechanism for securing said connection portions to the sample holder may also be used.

In a preferred embodiment of the invention the first wall and second wall each comprise an end portion, and wherein said the recess comprises a ceiling (i.e. a region of said bottom of the sample dish) which particularly integrally connects said end portions. I.e., in this embodiment, the first wall and the second wall are permanently connected to each other, e.g. glued or welded to each other or made from a single cast.

In an alternative second embodiment of the present invention, the sample holder comprises a first part and second part, wherein the first part is releasably connected to the first part, e.g. by a latching connection or another connection that does not involve a permanent connection method such as gluing or welding, wherein the first part comprises the first wall surrounding said opening for receiving and clamping the sample, and the second part comprises the second wall as well as a circumferential region of the bottom of the sample dish connected to an outer side of the second wall, wherein particularly the second wall comprises an end portion for connecting with the first part. Particularly, the first and second part of the sample holder may be connected to each other in a water-tight manner which may be achieved by means of a sealing element (e.g. O-ring).

Regarding said second embodiment, said first part preferably comprises a circumferential portion protruding from an end portion of the first wall, wherein said circumferential portion is designed to be connected to said end portion of the second wall of the second part, particularly such that said circumferential portion encompasses said end portion of the first wall (say with a circumferential region), and particularly engages with the first wall via a latching connection. In such a connected state, the first part also delimits said recess and forms a part of the bottom of the sample dish.

Further, the sample dish preferably comprises a circumferential wall protruding from a boundary of the bottom so that the sample dish can receive a liquid. This is particularly useful when the sample shall be immersed in a suitable buffer solution.

Furthermore, preferably, the first wall surrounding said opening for holding the sample particularly forms a tube and comprises an inner side, wherein said inner side comprises a particularly circumferential tooth or another suitable protrusion, wherein said tooth is inclined such that it encloses an acute angle with said inner side, such that said tooth presses against the sample when the latter is arranged in the opening, particularly when a force acting on the sample tends to push the sample into the opening. In other words, the toothed structure of the inner side of the first wall is contributing to hold the sample in place once it has been received by the sample holder. Other factors which contribute to the stabilization of the sample in a certain position in the sample holder are mechanical forces due to a discrete swelling of the lateral sides of samples within the sample holder opening after it exits the confined sample holder cylinder.

The sample holder or parts thereof are particularly made of a plastic, particularly Polypropylene, ABS, or Polytetrafluoroethylene and/or a metal, particularly, steel or aluminium.

Further, the sample holder may comprise a first and a second perfusion tube arranged in the bottom of the sample dish, wherein said first perfusion tube is for supplying the sample with a liquid medium and the second perfusion tube serves for drawing off liquid medium and particles from of the sample dish.

Particularly, a thin layer may be provided in each of the tubes, which seals the respective tube against liquids used for buffering the sample. These seals are particularly designed such that e.g. a needle from a syringe is able to penetrate and therefore provide a continuous connection with e.g. an external buffer supply or a waste reservoir. Particularly, for this reason, said tubes each comprise a first and a second end, wherein said tubes are particularly arranged such in the bottom of the sample dish that the first ends are arranged on an upper side of the bottom, e.g. on the side where a buffer solution for immersing the sample might be filled in the sample dish, and the second ends are arranged on the lower side of the bottom.

Furthermore, the problem underlying the present invention is solved by a sample holder system described herein.

According thereto, the sample holder system comprises a sample holder according to the invention, as well as a biopsy tool for collecting a sample, the biopsy tool comprising a cannula, wherein said cannula comprises a first end region for sampling a sample and an opposing second end region, wherein said second end region forms a connection portion, wherein said connection portion is connectable to e.g. the recess of the sample holder, wherein particularly said connection portion is releasably connectable to said recess of the sample holder, an elongated element being insertable into said cannula so as to push the sample from said first end region of the cannula to the second end region of said cannula and for pushing the sample from the second end into the opening of the sample holder when the sample holder and the biopsy tool are connected to each other. Furthermore, the sample holder system may comprise an AFM sample stage comprising a connection portion for (e.g. releasably) fastening the sample holder to the sample stage, wherein said connection portion of the sample stage may be insertable into said recess of the sample holder for connecting the sample holder (e.g. releasably) to the sample stage.

It is furthermore possible that the sample holder system comprises a temperature, gas and perfusion control system for controlling the temperature of the sample and for providing the sample with a gas and/or liquid (e.g. a buffer solution etc.).

Furthermore, the problem underlying the present invention is solved by a method for transferring a sample from a biopsy tool to a sample holder described herein.

According thereto, the method for transferring a sample from a biopsy tool to a sample holder (e.g. a sample holder according to the present invention), wherein said sample holder is particularly mountable on an AFM sample stage, comprises the steps of: providing a sample in a first end region of a cannula of a biopsy tool, wherein said cannula comprises a second end region opposing the first end region, which second end region forms a connection portion, attaching the biopsy tool to a sample holder (e.g. according to the invention) by inserting the connection portion of the biopsy tool into a recess of the sample holder, moving the sample from the first end region of the cannula towards the second end region of the cannula, particularly by inserting an elongated element into the cannula and pushing the sample from the first end region towards the second end region by means of said elongated element, pushing the sample out of the second end region of the cannula into an opening of the sample holder by means of the elongated element, which opening is aligned with the cannula, wherein the sample is clamped in said opening (e.g. the upper/top opening of the core cylinder of the sample holder). Particularly, releasing the biopsy tool from the sample holder, and particularly fastening the sample holder to a sample stage, particularly to a sample stage of an atomic force microscope, by inserting a connection portion of the sample stage into the recess of the sample holder.

In the following, embodiments of the present invention shall be described with reference to the Figures, wherein.

FIGS. 1 to 4 show a first embodiment of a sample holder according to the present invention. The sample holder comprises a circular bottom 2 comprising an opening 3 in its center which is encompassed by a first circumferential (e.g. cylindrical) wall 4 of the bottom 2, wherein said opening 3 is designed to receive and hold a sample 15. Further, the bottom 2 comprises a circumferential wall 7 which protrudes from an outer boundary and an upper side 2u of the bottom 2, such that the sample dish 1 may receive and hold a liquid such as a buffer solution for the sample 15. The bottom 2 further comprises a recess 8 which is delimited by a circumferential (e.g. cylindrical) second wall 5 of the bottom 2 encompassing said first wall 4, and by the first wall 4. Preferably, the first wall 4 is arranged coaxially with respect to the second wall 5. Further, the first and the second wall 4, 5 each comprise an end portion 4a, 5a, protruding from the upper side 2u of the bottom 2 (namely from a circumferential region 2a of the bottom 2 that is connected to an outer side 5o of the second wall), which end portions 4a, 5a are integrally connected to each other by an e.g. elevated central region 8a of the bottom 2 which also delimits said recess 8 and forms a boundary of said opening 3.

Figure 10:
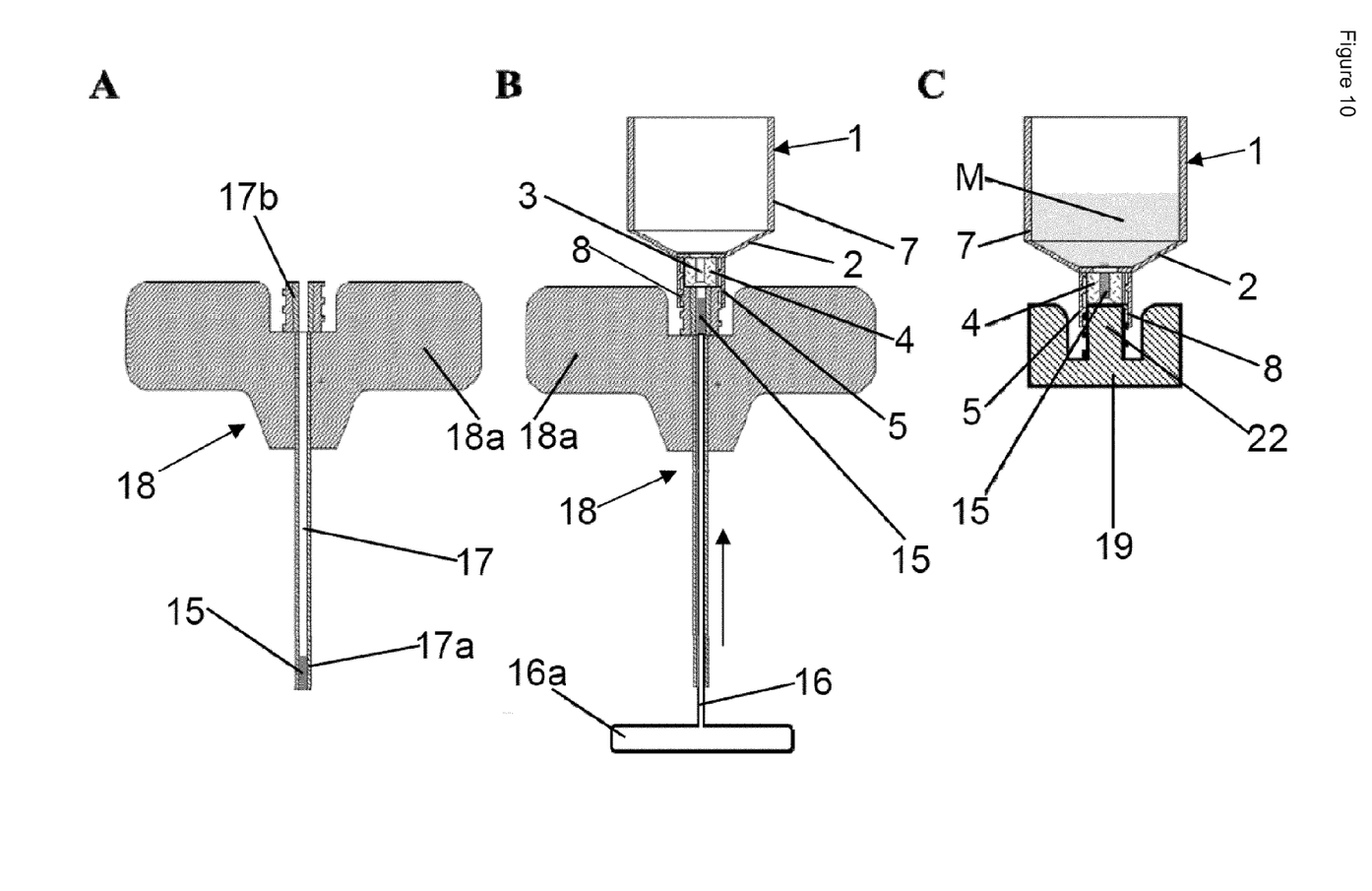
FIG. 10 shows the sample holder system according to the invention and illustrates the method for transferring a sample from a biopsy tool to a sample holder.

Furthermore, the second wall 5 comprises an inner side 5i which comprises a thread 6 for connecting with a biopsy tool 18 (cf. FIG. 10). Said biopsy tool 18 comprises an external thread on a connection portion 17b matching the inner thread 6 of the sample holder, such that the sample holder and the biopsy tool 18 can be releasably connected to each other by screwing said external thread in the thread 6 of the recess 8. Said internal thread 6 is particularly an ISO metric screw thread of size M12, which can be screwed on the connection portion 17b particularly comprising an external ISO metric screw thread of size M12 as well, such that the recess 8 and the connection portion 17b can be connected and fastened by screwing said external thread in said internal thread 6.

Preferably, the circumferential region 2a of the bottom 2 comprises a cone-like shape with an angle W1 with respect to a plane running perpendicular with respect to the longitudinal axis of the second wall 5, such that liquids tend to accumulate in the center of the sample dish 1. Further, the sample dish 1 comprises a first tube 9 and a second tube 10 for feeding a liquid into the sample dish 1 as well as for drawing such a liquid off the sample dish 1. For this, said tubes 9, 10 penetrate the bottom 2, preferably at an angle W3 and W4, respectively. The tubes 9, 10 are preferably arranged in the periphery of the bottom 2, preferably at an angle of W2 of 90° to each other.

An example for the dimensions of an integrally formed or one-piece sample holder as depicted in FIGS. 1 to 4 is given in table 1

TABLE 1

| Label | dimension in [mm] | Label | dimension in [°] |
|---|---|---|---|
| D1 | 40.00 | W1 | 9 |
| D2 | 1.00 | W2 | 90 |
| D3 | 7.12 | W3 | 15 |
| D4 | 7.16 | W4 | 2 |
| D5 | 2.22 | | |
| D6 | 6.27 | | |
| D7 | 3.20 | | |
| D8 | 0.50 | | |
| D9 | 14.00 | | |
| D10 | 1.01 | | |
| D11 | 4.79 | | |
| D12 | 12.00 | | |
| D13 | 8.00 | | |
| D14 | 3.40 | | |
| D15 | 1.90 | | |
| D16 | 7.52 | | |
| D17 | 9.06 | | |
| D18 | 16.00 | | |
| D19 | 17.00 | | |
| D20 | 14.00 | | |
| D21 | 4.86 | | |
| D22 | 17.01 | | |
| D23 | 6.19 | | |

Figure 1:
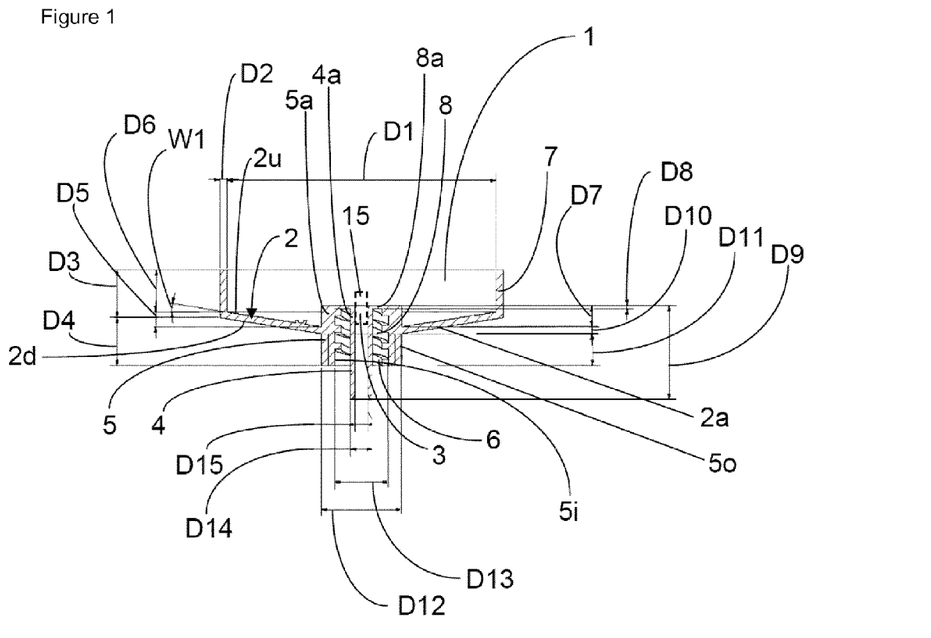
FIG. 1 shows a cross-section of a first embodiment of a sample holder according to the invention.
Figure 2:
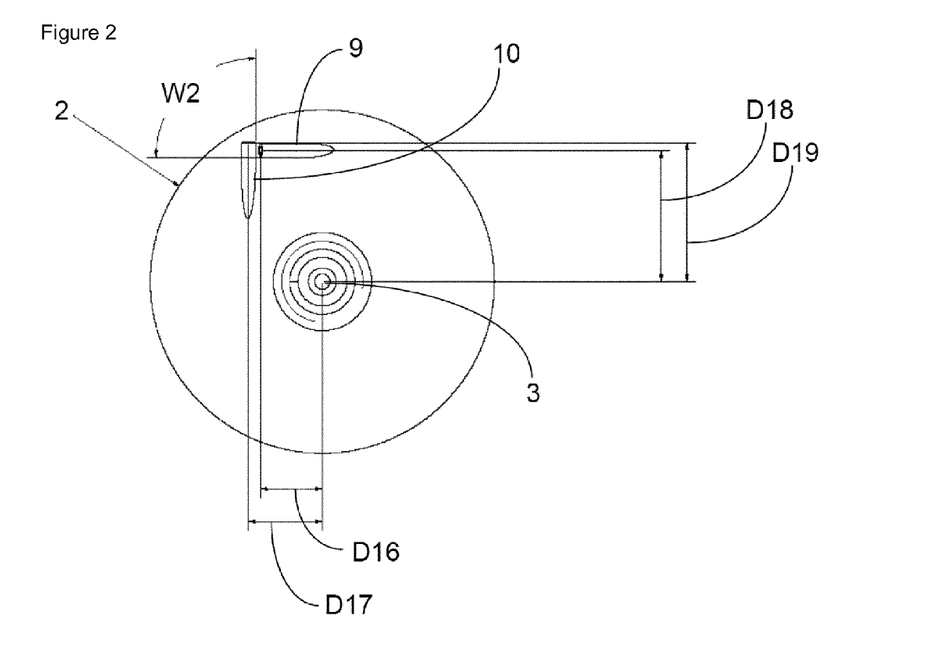
FIG. 2 shows plan view onto the sample holder shown in FIG. 1.
Figure 3:
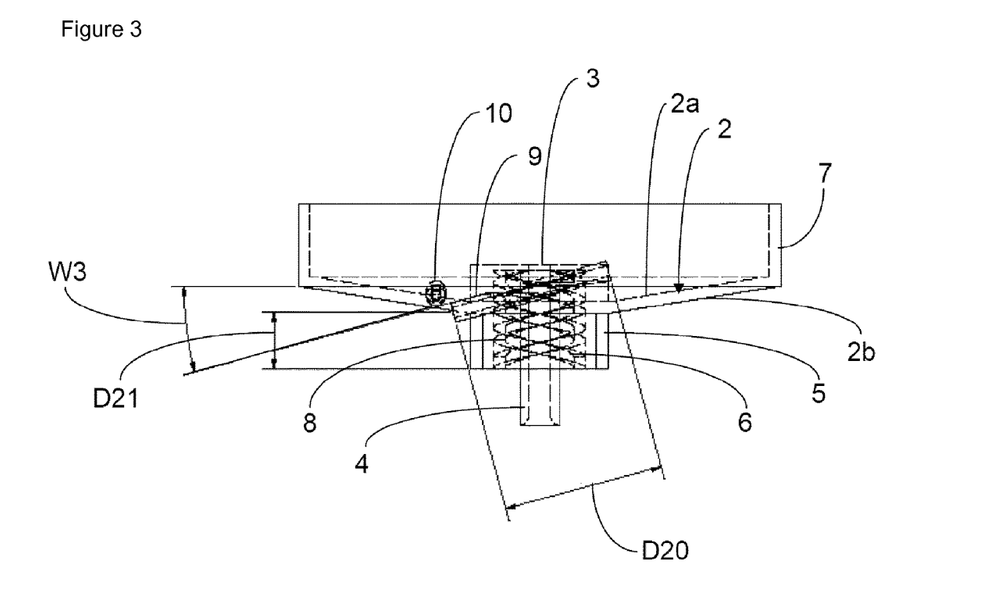
FIGS. 3-4 show cross-sectional views of the sample holder shown in FIGS. 1 and 2.
Figure 4:
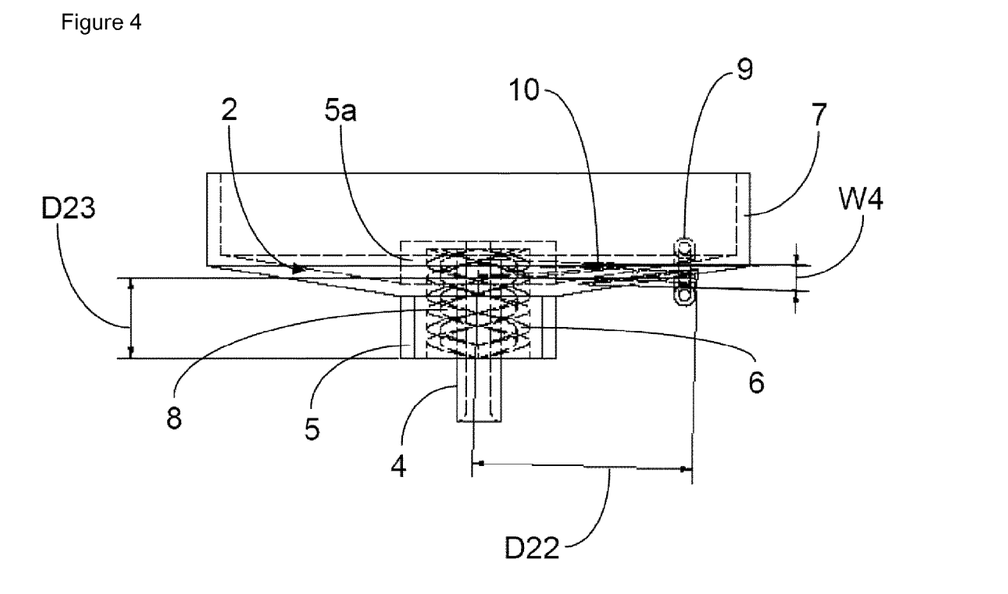
Figure 5:
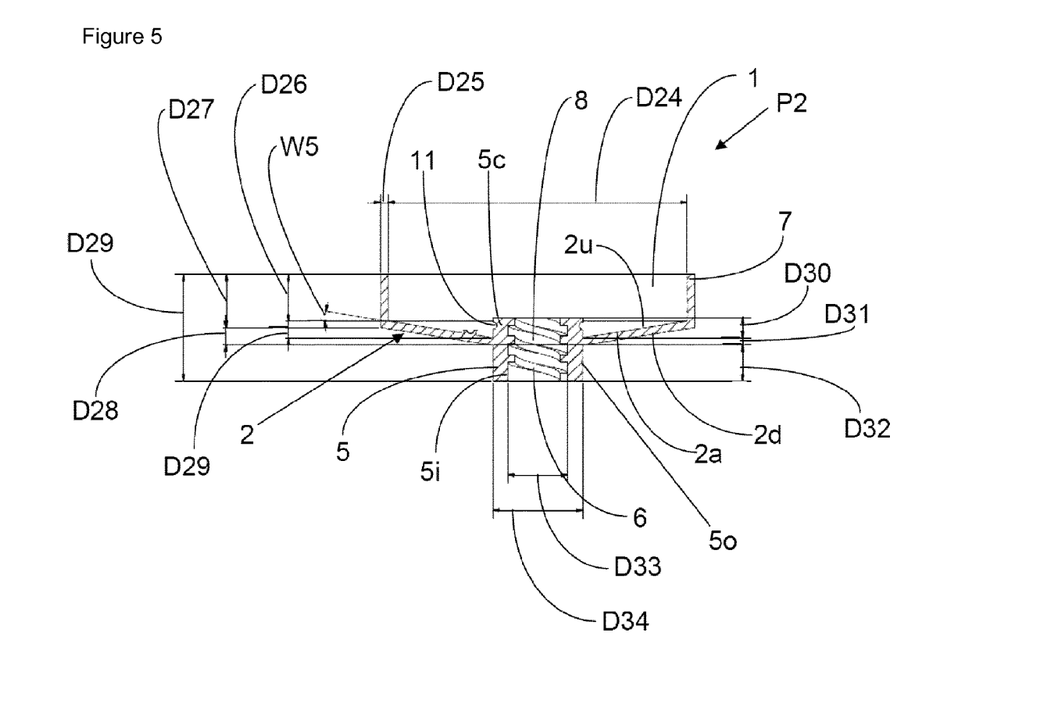
FIG. 5 shows a second part of a second embodiment of a sample holder according to the invention.
Figure 6:
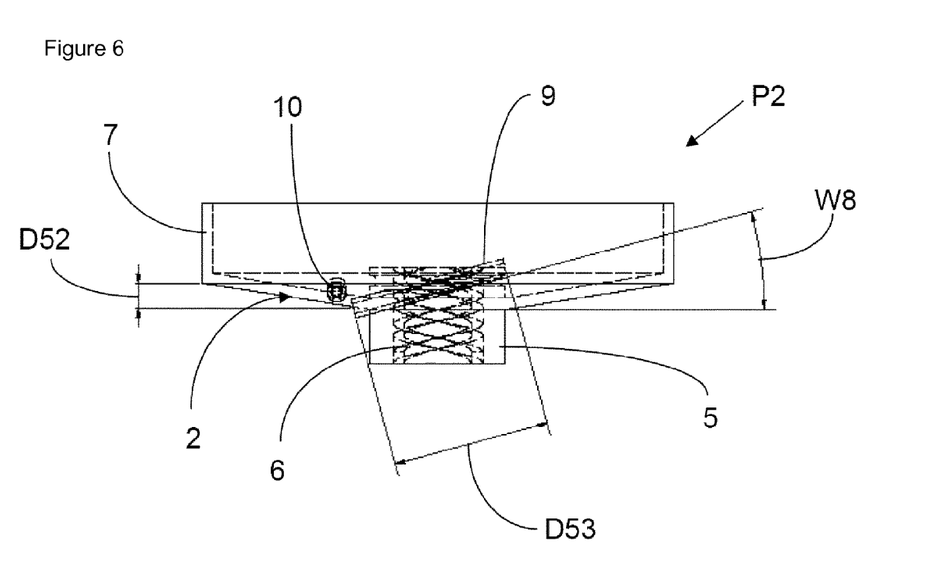
FIG. 6 shows a cross-sectional view of the second part shown in FIG. 5.
Figure 7:
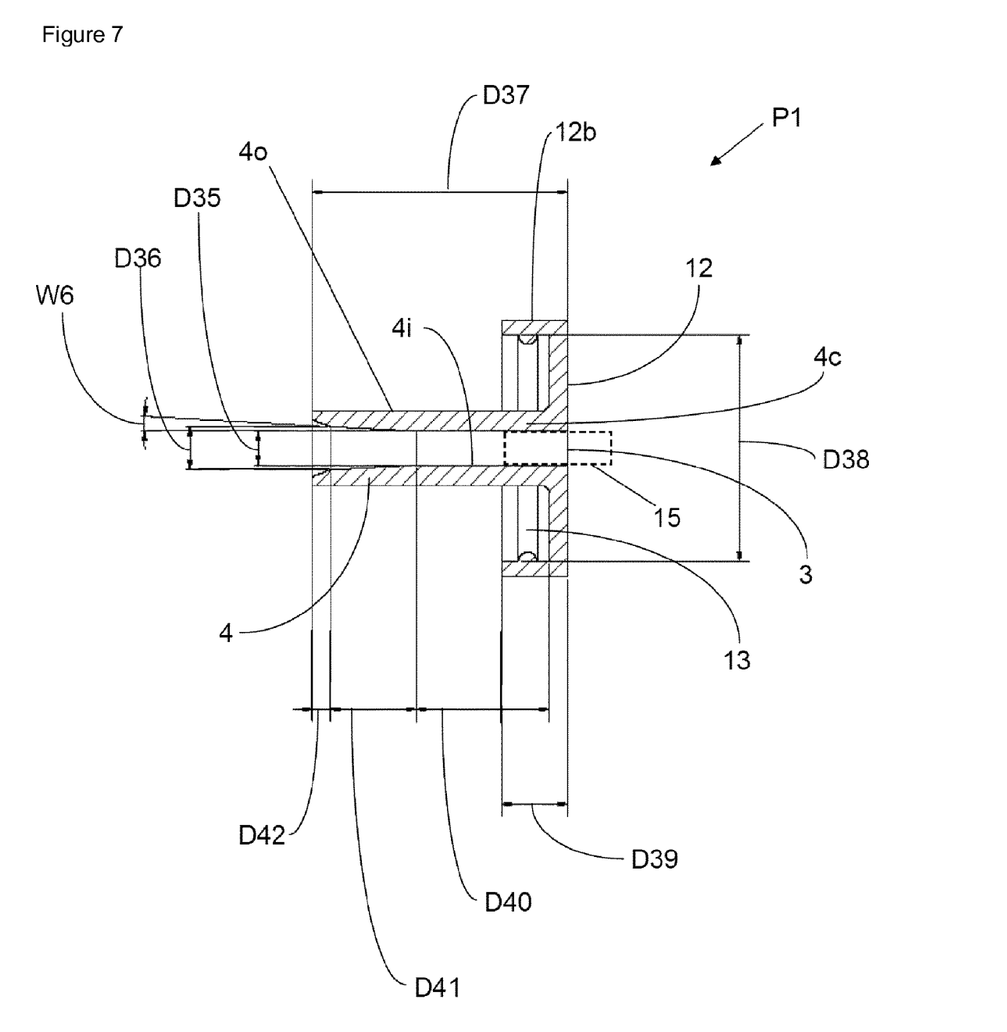
FIG. 7 shows a cross-sectional view of a first part of the sample holder according to the second embodiment.
Figure 8:
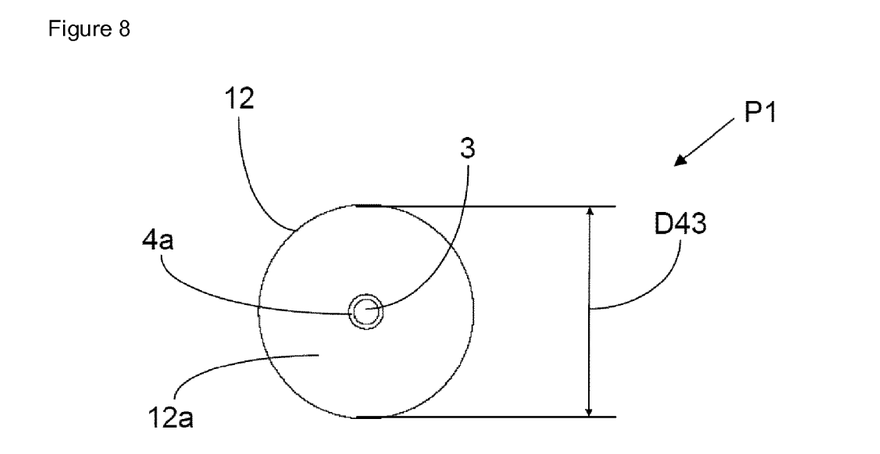
FIG. 8 shows a plan view onto the first part of the sample holder shown in FIG. 7.

FIGS. 5 to 8 show a further embodiment of the sample holder according to the invention, wherein said sample holder comprises a first part P1 and a second separate part P2, which are designed to be connected to each other in a releasable manner (i.e. such that they can be released from each other non-destructively). This is particularly preferable since said first part P1 (as shown in FIG. 7 and FIG. 8) might be disposed after use of the sample holder, whereas the second part P2 (shown in FIGS. 5 and 6) might be re-used for further measurements on another sample 15.

The second part P2 comprises a circumferential region 2a of a bottom 2 of the sample dish 1, which region 2a is connected to an outer side 5o of a second wall 6 of bottom 2, which encompasses a recess 8 of the sample holder, which—in an unassembled state, i.e. without the first part P1 of the sample holder—forms a through-hole. Said second wall 5 further comprises an inner side 5i facing away from said outer side 5a, which comprises an (internal) thread 6, particularly an ISO metric screw thread of size M12 for being screwed on an external thread of a connection portion 22, 17b of sample stage 19 or a biopsy tool 18. Said connection portions 17b, 22 particularly comprise an external ISO metric screw thread of size M12 as well (see also above).

Furthermore, the second part P2 of the sample holder comprises a circumferential wall 7 protruding from an outer boundary of the bottom 2, as well as a perfusion tubing comprising tubes 9, 10 as before (see above).

For connecting the first part P1 to the second part P2 of the sample holder, the first part P1 comprises a circumferential portion 12 protruding radially from an end portion 4c of the first wall 4, wherein said protruding portion 12 of the first wall 4 comprises a circumferential boundary region 12b with a circumferential protrusion 13 facing an outer side 4o of said first wall 4, which protrusion 13 is designed to form-fittedly engage with a circumferential groove formed in an outer side of the second wall's 5 end portion 5c, so as to connect the first part P1 to the second part P2. In this assembled state, the protruding circumferential portion 12 encompasses with its boundary region 12b the second wall 5 of the second part P2, particularly in a sealing manner.

Said circumferential portion 12 of the first wall 4 may comprise the shape of disk comprising a rim 12b projecting from the outer boundary of said disk, which also delimits or closes said recess 8 when the first and the second part P1, P2 are assembled as intended.

The inner diameter D35 of the first wall 4 is preferably chosen such that a sample 15 is receivable from e.g. a biopsy tool 18 whose cannula 17 has approximately the same inner diameter.

Exemplary dimensions for a sample holder comprising two separable parts P1, P2 are listed in the table 2:

TABLE 2

| Label | dimension in [mm] | Label | dimension in [°] |
|---|---|---|---|
| D24 | 40.00 | W5 | 9 |
| D25 | 1.00 | W6 | 3 |
| D26 | 6.27 | W8 | 15 |
| D27 | 7.12 | | |
| D28 | 2.38 | | |
| D29 | 2.22 | | |
| D30 | 2.70 | | |
| D31 | 1.01 | | |
| D32 | 4.79 | | |
| D33 | 8.00 | | |
| D34 | 12.00 | | |
| D35 | 1.80 | | |
| D36 | 2.29 | | |
| D37 | 13.50 | | |
| D38 | 12.00 | | |
| D39 | 3.50 | | |
| D40 | 7.00 | | |
| D41 | 4.53 | | |
| D42 | 0.97 | | |
| D43 | 13.60 | | |
| D52 | 2.30 | | |
| D53 | 14.00 | | |

Figure 9:
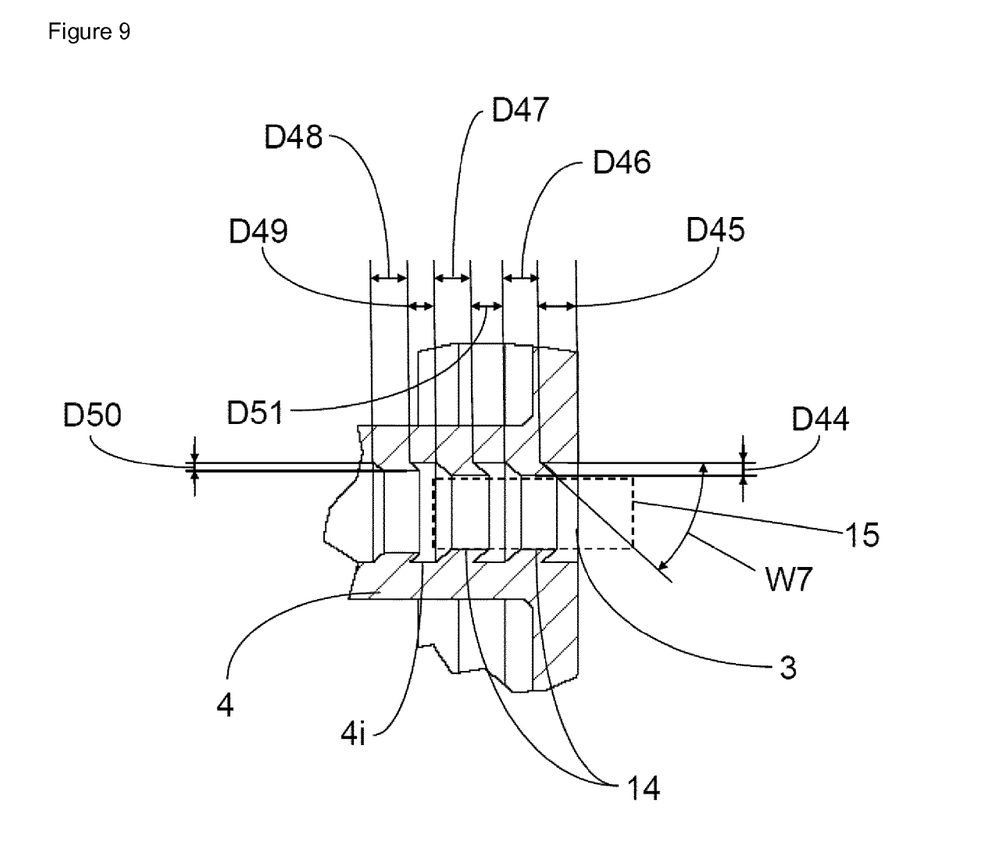
FIG. 9 shows a detail of a sample holder according to the invention.

Further, FIG. 9 shows a detailed view of an embodiment of said first wall 4 that may be used for both sample holders describes above. Here, the first wall 4 comprises an inner side 4i which comprises circumferential teeth 14, which are inclined (i.e. project under an acute angle from said inner side 4i). Said teeth point 14 point towards said opening 3 on the upper side 2u of the bottom such that a sample 15, which is arranged in said opening 3 resists being pushed further inside said opening 3.

Exemplary dimensions for the detail depicted in FIG. 9 are listed in table 3:

TABLE 3

| Label | dimension in [mm] | Label | dimension in [°] |
|---|---|---|---|
| D44 | 0.30 | W7 | 40 |
| D45 | 0.80 | | |
| D46 | 0.80 | | |
| D47 | 0.80 | | |
| D48 | 0.80 | | |
| D49 | 0.58 | | |
| D50 | 0.20 | | |
| D51 | 0.70 | | |

FIG. 10 schematically shows a sample holder system according to the invention as well as the method for transferring a sample 15 from a biopsy tool 18 to a sample holder and subsequently to a sample stage 19.

In FIG. 10A the biopsy tool 18 is depicted comprising a cannula 17, which has two opposing end regions 17a, 17b, one for sampling during biopsy (17a) and the other one (17b) for forming a connection portion for connecting the biopsy tool 18 to the recess 8 of the sample holder.

Initially, after obtaining a sample 15, the latter is located in the first end region 17a of the cannula 17. In a second step, which is depicted in FIG. 10B, the biopsy tool 18 is connected with its connection portion 17b to the recess 8 of the sample holder. This connection is particularly established via a screw coupling as described above. An elongated element 16 matching the interior of the cannula 17 is then inserted into the cannula 17 at the first end region 17a and the sample 15 is pushed beyond the connection portion 17b of the biopsy tool 18 into said opening 3 of the sample holder which is aligned with the cannula 17 when the latter is fastened to the sample holder as intended. In a last step, depicted in FIG. 10C, the biopsy tool 18 is released from the sample holder and the sample holder is attached to a connection portion 22 of a sample stage 19. This connection is particularly also established via said screw coupling described before. Other coupling mechanisms are also possible.

The invention claimed is:

1. A sample holder for holding a sample (15) for an atomic force microscope
   characterized by
   a sample dish (1) comprising a bottom (2), and
   an opening (3) arranged in said bottom (2) for receiving and holding the sample (15), wherein said opening (3) is encompassed by a circumferential first wall (4) of said bottom (2) that is designed to clamp said sample (15) when the sample (15) is received by said opening (3).

2. The sample holder according to claim 1, characterized in that said circumferential first wall is at least in sections formed out of a hydrophilic polymer, which expands in contact with water and/or a buffer solution, so that the inner diameter of said opening (3) decreases for clamping the sample (S) when brought into contact with said water and/or buffer solution.

3. The sample holder according to claim 1, characterized in that the bottom (2) comprises a recess (8) delimited by a circumferential second wall (5) of the bottom (2) and said circumferential first wall (4), wherein said circumferential second wall (5) encompasses said circumferential first wall (4).

4. The sample holder according to claim 3, characterized in that said recess (8) is designed to receive a connection portion (22) of a sample stage (19) of an atomic force microscope, for fastening the sample holder to the sample stage (19).

5. The sample holder according to claim 3, characterized in that said recess (8) is designed to receive a connection portion (17b) of a biopsy tool (18) for collecting the sample (15) and transferring said sample (15) to the sample holder.

6. The sample holder according to claim 3, characterized in that said circumferential second wall (5) comprises an inner side (5i), wherein said inner side (5i) comprises a thread (6) for receiving a connection portion (22) of a sample stage (19) and/or a connection portion (17b) of a biopsy tool (18).

7. The sample holder according to claim 3, characterized in that the first wall (4) and second wall (5) each comprise a circumferential end portion (4a, 5a), and wherein the recess (8) is further delimited by a region (8a) of the bottom (2) which connects said end portions (4a, 5a).

8. The sample holder according to claim 3, characterized in that the sample holder comprises a first part (P1) and a separate second part (P2), wherein the first part (P1) is designed to be releasably connected to the second part (P2), wherein the first part (P1) comprises the first wall (4) surrounding the opening (3) and the second part (P2) comprises the second wall (5) and a circumferential region (2a) of the bottom (2) being connected to an outer side (5o) of the second wall (5), wherein the second wall (5) comprises an end portion (5c) for connecting with the first part (P1).

9. The sample holder according to claim 8, characterized in that the first part (P1) comprises a circumferential portion (12) protruding from an end portion (4c) of the first wall (4), wherein said circumferential portion (12) is designed to be releasably connected to said end portion (5c) of the second wall (5) of the second part (P2), by means of a latching connection such that said circumferential portion (12) encompasses said end portion (5c) of the second wall (5).

10. The sample holder according to claim 1, characterized in that the sample dish (1) comprises a circumferential wall (7) protruding from a boundary of the bottom (2) of the sample dish (1).

11. The sample holder according to claim 1, characterized in that the first wall (4) surrounding the opening (3) comprises an inner side (4i), wherein said inner side (4i) comprises a circumferential tooth (14), wherein said tooth (14) is inclined such that it encloses an acute angle (W7) with said inner side (4i), such that said tooth (14) presses against the sample (15) when the sample (15) is arranged in the opening (3) so as to clamp the sample (15) in the opening (3).

12. The sample holder according to claim 1, characterized in that a first perfusion tube (9) and a second perfusion tube (10) are arranged in the bottom (2) of the sample dish, wherein said first perfusion tube (9) is designed for supplying the sample with a liquid medium (M), and wherein the second perfusion tube (10) is designed for drawing off liquid medium (M) and/or particles from the sample dish (1).

13. A sample holder system comprising a sample holder according to claim 1, wherein the sample holder system further comprises:
a biopsy tool (18) for collecting a sample (15), which biopsy tool (18) comprises a cannula (17), wherein said cannula (17) comprises a first end region (17a) for sampling a sample and an opposing second end region (17b), wherein said second end region (17b) forms a connection portion (17b) for connecting the biopsy tool (18) to the sample holder, wherein said connection portion (17b) is designed to be inserted into a recess (8) of the sample holder in order to connect the biopsy tool (18) to the sample holder,
an elongated element (16) being designed to be inserted into said cannula (17) so as to push a sample (15) from said first end region (17a) of the cannula (17) to the second end region (17b) of said cannula (17), and for moving the sample (15) from the second end region (17b) to the opening (3) of the sample holder when the biopsy tool (18) is connected to the sample holder, and
a sample stage (19) for an atomic force microscope, wherein said sample stage (19) comprises a connection portion (22) that is designed to be connected to the sample holder, wherein said connection portion (22) is designed to be inserted into said recess (8) of the sample holder in order to connect the sample holder to the sample stage (19).

14. A method for transferring a sample from a biopsy tool to a sample holder, according to claim 1, comprising the steps of:
providing a sample (15) in a first end region (17a) of a cannula (17) of a biopsy tool (18), wherein said cannula (17) comprises a second end region (17b) opposing the first end region (17a), which said second end region (17b) forms a connection portion,
attaching the biopsy tool (18) to a sample holder by inserting the connection portion (17b) of the biopsy tool (18) into a recess (8) of the sample holder,
moving the sample (15) from the first end region (17a) of the cannula (17) towards the second end region (17b) of the cannula (17), by inserting an elongated element (16) into the cannula (17) and pushing the sample from the first end region (17a) towards the second end region (17b),
pushing the sample (15) out of the second end region (17b) of the cannula into an opening (3) of the sample holder, which said opening (3) is aligned with the cannula (17), wherein the sample is clamped in said opening (3),
releasing the biopsy tool (18) from the sample holder, and
fastening the sample holder to a sample stage (19) of an atomic force microscope, by inserting a connection portion (22) of the sample stage (19) into the recess (8) of the sample holder.

* * * * *